United States Patent [19]

Becker et al.

[11] 4,422,864

[45] Dec. 27, 1983

[54] CYCLOHEXANEDIONE DERIVATIVES, THEIR PREPARATION AND HERBICIDES CONTAINING THEM

[75] Inventors: Rainer Becker, Bad Durkheim; Dieter Jahn, Neckarhausen; Wolfgang Rohr, Wachenheim; Walter Himmele, Walldorf; Hardo Siegel, Speyer; Bruno Wuerzer, Otterstadt, all of Fed. Rep. of Germany

[73] Assignee: BASF Aktiengesellschaft, Fed. Rep. of Germany

[21] Appl. No.: 380,469

[22] Filed: May 20, 1982

[30] Foreign Application Priority Data

May 29, 1981 [DE] Fed. Rep. of Germany ....... 3121355

[51] Int. Cl.³ .......................... A01N 9/12; A01N 9/20; C07D 309/04; C07D 333/22
[52] U.S. Cl. .......................................... 71/88; 71/90; 549/13; 549/39; 549/373; 549/426; 549/451; 549/491; 549/347
[58] Field of Search ...................... 71/88, 90; 549/426, 549/373, 39, 451, 13, 491, 347

[56] References Cited

U.S. PATENT DOCUMENTS 3,989,737 11/1976 Sawaki et al. ........................... 71/90
4,008,067 2/1977 Hirono et al. ....................... 549/417

FOREIGN PATENT DOCUMENTS 1461170 1/1977 United Kingdom ................... 71/80

Primary Examiner—Nicky Chan
Attorney, Agent, or Firm—Keil & Witherspoon

[57] ABSTRACT

Cyclohexanedione derivatives of the general formula

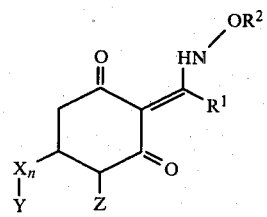

where $R^1$ is alkyl, $R^2$ is alkyl, alkenyl, alkynyl or haloalkenyl, X is alkylene, n is 0 or 1, Y is a heterocyclic radical and Z is hydrogen or methoxycarbonyl, and salts of these compounds are used in herbicides.

6 Claims, No Drawings

CYCLOHEXANEDIONE DERIVATIVES, THEIR PREPARATION AND HERBICIDES CONTAINING THEM

The present invention relates to novel cyclohexane-1,3-dione derivatives, processes for the preparation of these compounds, and herbicides containing them.

German Published Application DAS 2,439,104 discloses cyclohexanedione derivatives substituted by thienyl or furyl in the 5-position which have a relatively weak herbicidal action.

We have found that compounds of the general formula I

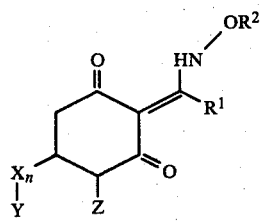

where $R^1$ is alkyl of 1 to 4 carbon atoms, $R^2$ is alkyl of 1 to 4 carbon atoms, alkenyl of 3 or 4 carbon atoms, alkynyl of 3 or 4 carbon atoms or haloalkenyl of 3 or 4 carbon atoms and 1 to 3 halogen atoms, X is straight-chain or branched alkylene of 1 to 5 carbon atoms, which is unsubstituted or substituted by phenyl, n is 0 or 1, Y is a non-aromatic heterocyclic radical of 4 to 7 atoms and not more than one double bond in the heterocyclic ring, which contains 1 or 2 hetero-atoms from the group comprising sulfur, nitrogen and oxygen in any desired sequence and is unsubstituted or substituted by alkyl, and Z is hydrogen or methoxycarbonyl, and the salts of these compounds are particularly useful for controlling undesirable plants from the Gramineae family and at the same time, as selective herbicides, are very well tolerated by broad-leaved crops and other crops which do not belong to the Gramineae family.

Examples of $R^1$ are propyl, ethyl and butyl, examples of $R^2$ are methyl, ethyl, propyl, allyl, 2-chloroallyl and 3-chloroallyl, examples of X are methylene and ethylene and examples of Y are tetrahydropyranyl, dihydropyranyl, methyltetrahydropyranyl, dioxanyl, dioxolanyl, dithiolanyl, dihydrothiopyranyl tetrahydrothiopyranyl, dimethyldihydropyranyl, tetrahydrofuranyl and dimethyldihydrothiopyranyl.

The novel compounds can exist in various tautomeric forms:

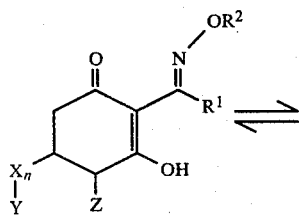 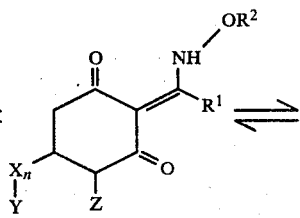

The present invention includes all these forms.

The novel compounds can be prepared, for example, as follows:

(a) A compound II is reacted with a compound of the formula $R_2ONH_3^+A^-$ according to the equation

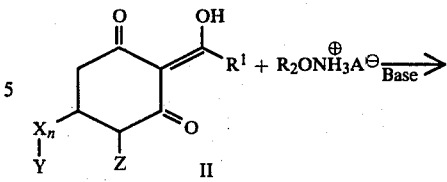

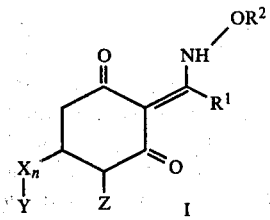

where $R^1$, $R^2$, X, Y, Z and A have the above meanings.

The reaction is advantageously carried out in a heterogeneous phase system in an inert solvent at from 0° to 80° C. in the presence of a base, for example a carbonate, bicarbonate, acetate, alcoholate, hydroxide or oxide of an alkali metal or alkaline earth metal, especially of sodium, potassium, magnesium or calcium. Organic bases such as pyridine or tertiary amines can also be used.

A pH range from 2 to 7, in particular from 4.5 to 5.5, is especially suitable for the reaction. The pH range is advantageously established by the addition of an acetate, for example an alkali metal acetate, in particular sodium or potassium acetate, or mixtures thereof, for example in amounts of from 0.5 to 2 moles, per mole of ammonium compound.

Examples of suitable solvents are methanol, ethanol, isopropanol, benzene, tetrahydrofuran, chloroform, acetonitrile, dichloroethane, ethyl acetate, dioxane and dimethylsulfoxide.

The reaction takes some hours, and the product can be isolated by concentrating the mixture, adding water, extracting the mixture with a non-polar solvent and distilling off the solvent under reduced pressure.

(b) The novel compounds can moreover be prepared by reacting a compound II with the corresponding amine $R^2$-$ONH_2$.

(c) The novel derivatives can furthermore be prepared by alkylating an oxime with an alkylating agent:

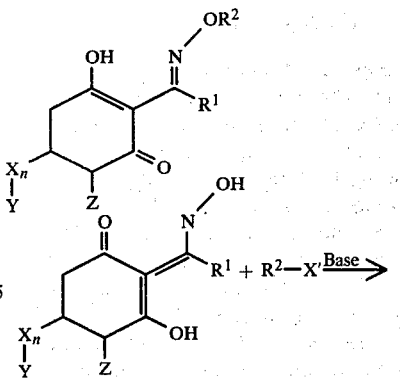

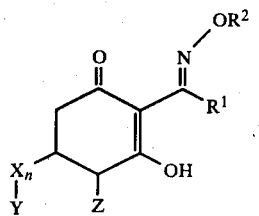

Process (a) is preferred.

The compounds of the formula II can be obtained by acylating a cyclohexane-1,3-dione III, as described in Tetrahedron Lett. 29, 2,491. The compounds III can also exist in tautomeric forms:

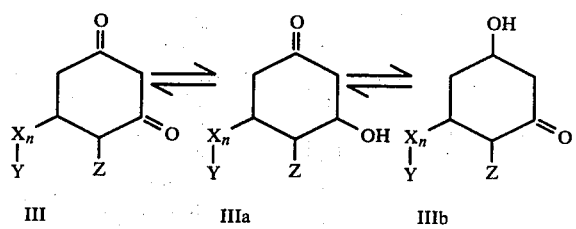

Compounds of the formula III can be prepared from an aldehyde $Y-X_n-CH=O$ in a conventional manner, for example by aldol condensation with a ketone and subsequent cyclization with a malonate by a method similar to that in Organic Synthesis Coll. II, 200, or by reacting the aldehyde $Y-X_n-CH=O$ with malonic acid by the Knoevenagel-Döbner method (cf. Org. Reaktions 15, 204), esterification of the resulting acid and cyclization with ethyl acetate in a manner similar to that described, for example, in Chem. Ber. 96, 2,946.

Examples of salts of the compounds are the alkali metal salts, in particular the sodium or potassium salts.

The sodium and potassium salts of the novel compounds can be obtained by treating these compounds with sodium hydroxide or potassium hydroxide in aqueous solution or in an organic solvent, such as methanol, ethanol or acetone. Alkali metal alcoholates can also be used as bases.

Other metal salts, for example the manganese, copper, zinc, iron or barium salts, can be prepared from the sodium salts by reaction with the corresponding metal chloride in aqueous solution. In the Examples which follow and which illustrate the preparation of the novel cyclohexanediones, parts by weight bear the same relation to parts by volume as that of the kilogram to the liter.

EXAMPLE 1

10.0 parts by weight of 2-butyryl-4-methoxycarbonyl-5-[tetrahydropyran-4-ylmethyl]-cyclohexane-1,3-dione were dissolved in 150 parts by volume of ethanol, and 2.93 parts by weight of ethoxyammonium chloride and 2.71 parts by weight of anhydrous sodium acetate were added. The mixture was stirred at 20° C. for 20 hours, poured into ice-water and extracted with methylene chloride. The organic phase was concentrated to give 10.5 parts by weight of 2-(1-ethoxyaminobutylidene)-4-methoxycarbonyl-5-[tetrahydropyran-4-ylmethyl]-cyclohexane-1,3-dione (compound No. 1) as a viscous oil having the following structure:

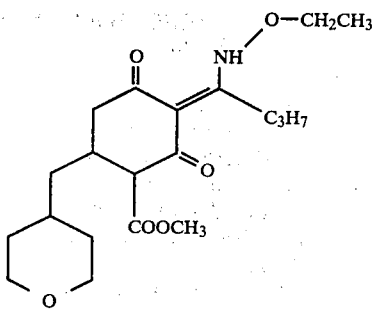

$C_{20}H_{31}O_6N$, molecular weight=381. Calculated: C 63.0, H 8.2, N 3.7. Found: C 63.3, H 8.1, N 3.7.

EXAMPLE 2

10.0 parts by weight of 2-butyryl-5-[2-(1,3-dioxan-2-yl)-ethyl]-cyclohexane-1,3-dione were dissolved in 150 parts by volume of ethanol, 3.72 parts by weight of allyloxyammonium chloride and 3.03 parts by weight of anhydrous sodium acetate were added, and the mixture was stirred at 20° C. for 20 hours. The suspension was then stirred into ice-water and extracted with methylene chloride. The organic phase was concentrated to give 11.5 parts by weight of 2-(1-allyloxyaminobutylidene)-5-[2-(1,3-dioxan-2-yl)-ethyl]-cyclohexane-1,3-dione (compound No. 2) as a solid having the following structure (melting point: 50°–52° C.):

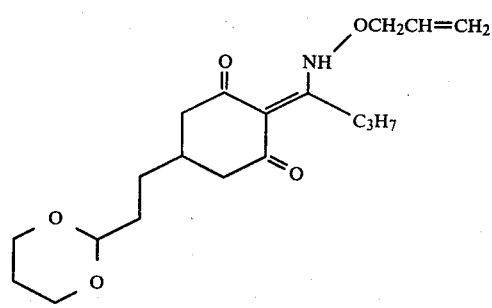

$C_{19}H_{29}O_5N$, molecular weight=351. Calculated: C 64.9, H 8.3, N 4.0. Found: C 65.1, H 8.1, N 3.7.

EXAMPLE 3

12.0 parts by weight of 2-butyryl-4-methoxycarbonyl-5-[2-(1,3-dithiolan-2-yl)-ethyl]-cyclohexane-1,3-dione were dissolved in 150 parts by volume of ethanol, and 3.29 parts by weight of allyloxyammonium chloride and 3.28 parts by weight of anhydrous sodium acetate were added. The mixture was stirred at 20° C. for 20 hours, poured onto ice-water and extracted with methylene chloride. The organic phase was concentrated to give 13.1 parts by weight of 2-(1-allyloxyaminobutylidene)-4-methoxycarbonyl-5-[2-(1,3-dithiolan-2-yl)-ethyl]-cyclohexane-1,3-dione (compound No. 3) as a viscous oil having the following structure:

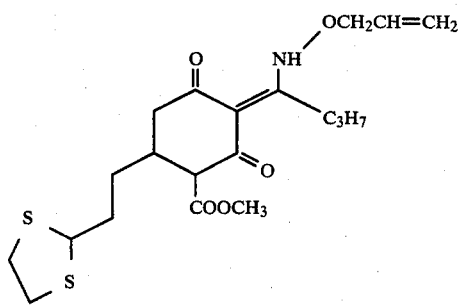

$C_{20}H_{29}O_5NS_2$, molecular weight=427. Calculated: C 56.2, H 6.8, N 2.3, S 15.0. Found: C 57.0, H 6.7, N 2.8, S 14.7.

The following compounds were obtained in a corresponding manner:

| Compound no. | R¹ | R² | $X_n$—Y | Z | M.p. or refractive index |
|---|---|---|---|---|---|
| 4 | Propyl | Allyl | Tetrahydropyran-4-yl-methyl | COOCH₃ | |
| 5 | " | Ethyl | " | H | |
| 6 | " | Allyl | " | H | |
| 7 | " | Allyl | 2-(1,3-Dioxan-2-yl-)ethyl | COOCH₃ | |
| 8 | " | Ethyl | " | H | |
| 9 | " | Allyl | 4-Methyltetrahydropyran-3-yl | COOCH₃ | |
| 10 | " | Ethyl | " | H | $n_D^{22}$ 1.5235 |
| 11 | " | Allyl | " | H | $n_D^{22}$ 1.5297 |
| 12 | " | Ethyl | 1-(4-Methyl-1,3-dioxan-2-yl-)2-methyl-propyl | COOCH₃ | |
| 13 | " | Allyl | 1-(4-Methyl-1,3-dioxan-2-yl-)2-methyl-propyl | COOCH₃ | |
| 14 | " | Ethyl | 1-(4-Methyl-1,3-dioxan-2-yl-)2-methyl-propyl | H | |
| 15 | " | Ethyl | 1-Phenyl-2-(1,3-dioxolan-2-yl-)ethyl | COOCH₃ | |
| 16 | " | Allyl | 1-Phenyl-2-(1,3-dioxolan-2-yl-)ethyl | COOCH₃ | |
| 17 | " | Ethyl | (2-H)—5,6-Dihydropyran-3-yl | COOCH₃ | |
| 18 | " | Allyl | " | COOCH₃ | |
| 19 | " | Ethyl | " | H | $n_D^{20}$ 1.5339 |
| 20 | " | Ethyl | (4-H)—2,3-Dihydropyran-2-yl | COOCH₃ | $n_D^{26}$ 1.5225 |
| 21 | " | Allyl | (4-H)—2,3-Dihydropyran-2-yl | COOCH₃ | $n_D^{27}$ 1.5262 |
| 22 | " | Ethyl | Tetrahydropyran-2-yl | COOCH₃ | $n_D^{24}$ 1.5142 |
| 23 | " | Allyl | " | COOCH₃ | $n_D^{25}$ 1.5204 |
| 24 | " | Ethyl | " | H | $n_D^{26}$ 1.5136 |
| 25 | " | Allyl | " | H | $n_D^{27}$ 1.5200 |
| 26 | " | Ethyl | Tetrahydro-pyran-3-yl | H | $n_D^{24}$ 1.5149 |
| 27 | " | 3-Chloroallyl | Tetrahydropyran-4-ylmethyl | COOCH₃ | 75–79° |
| 28 | " | 2-Chloroallyl | " | COOCH₃ | 72–75° |
| 31 | " | 3-Chloroallyl | " | H | |
| 32 | " | 2-Chloroallyl | " | H | |
| 36 | " | " | 2-(1,3-Dioxan-2-yl-)ethyl | H | 55–58° |
| 37 | " | 3-Chloroallyl | 2-(1,3-Dioxan-2-yl-)ethyl | H | $n_D^{22}$ 1.5281 |
| 38 | " | 2,3,3-Trichloroallyl | " | H | $n_D^{22}$ 1.5401 |
| 41 | " | 3-Chloroallyl | 4-Methyltetrahydropyran-3-yl | H | $n_D^{22}$ 1.5389 |
| 44 | " | Allyl | 1-Phenyl-2-(1,3-dioxolan-2-yl-)ethyl | H | |
| 48 | " | Ethyl | (4-H)—2,5-Dimethyl-2,3-dihydropyran-2-yl | H | $n_D^{18}$ 1.5259 |
| 49 | " | Allyl | (4-H)—2,5-Dimethyl-2,3-dihydropyran-2-yl | H | $n_D^{18}$ 1.5301 |
| 61 | " | Ethyl | (2-H)—5,6-Dihydrothiopyran-3-yl | H | $n_D^{23}$ 1.5620 |
| 62 | " | Allyl | " | H | $n_D^{23}$ 1.5678 |
| 65 | " | Ethyl | (2-H)—2,6-Dimethyl-5,6-dihydrothiopyran-3-yl | H | $n_D^{23}$ 1.5464 |
| 66 | " | Allyl | (2-H)—2,6-Dimethyl-5,6-dihydrothiopyran-3-yl | H | $n_D^{23}$ 1.5510 |
| 68 | " | 2,3,3-Trichloroallyl | 4-Methyltetrahydropyran-3-yl | H | |
| 71 | " | Propargyl | " | H | $n_D^{23}$ 1.5332 |
| 72 | " | Propyl | " | H | $n_D^{26}$ 1.5181 |
| 76 | " | Allyl | (2-H)—5,6-Dihydropyran-3-yl | H | $n_D^{18}$ 1.5449 |
| 77 | Ethyl | Ethyl | Tetrahydropyran-2-yl | H | $n_D^{31}$ 1.5199 |
| 78 | " | Allyl | " | H | $n_D^{31}$ 1.5265 |
| 79 | Propyl | Allyl | Tetrahydropyran-3-yl | H | $n_D^{18}$ 1.5313 |
| 80 | Ethyl | Ethyl | " | H | 38–40° |
| 81 | Ethyl | Allyl | " | H | $n_D^{18}$ 1.5342 |
| 83 | " | Ethyl | (2-H)—2,6-Dimethyl-5,6-dihydrothiopyran-3-yl | H | $n_D^{23}$ 1.5549 |
| 84 | " | Allyl | (2-H)—2,6-Dimethyl-5,6-dihydrothiopyran-3-yl | H | $n_D^{23}$ 1.5608 |
| 85 | " | Ethyl | (2-H)—5,6-Dihydrothiopyran-3-yl | H | $n_D^{23}$ 1.5689 |
| 86 | " | Allyl | " | H | $n_D^{23}$ 1.5727 |
| 91 | Propyl | Ethyl | Tetrahydrofuran-2-yl | H | $n_D^{21}$ 1.5179 |

-continued

| Compound no. | R¹ | R² | $X_n$—Y | Z | M.p. or refractive index |
|---|---|---|---|---|---|
| 92 | " | Allyl | " | H | $n_D^{21}$ 1.5261 |
| 99 | " | Ethyl | (2-H)—2,6-Dimethyl-5,6-dihydropyran-3-yl | H | $n_D^{29}$ 1.5149 |
| 100 | " | Allyl | (2-H)—2,6-Dimethyl-5,6-dihydropyran-3-yl | H | $n_D^{29}$ 1.5275 |
| 112 | Sodium salt of compound no. 26 | | | | 168–172° (decomposes) |

The following compounds may be obtained analogously:

| Compound no. | R¹ | R² | $X_n$—Y | Z |
|---|---|---|---|---|
| 29 | Propyl | 2,3,3-Trichloroallyl | Tetrahydropyran-4-ylmethyl | COOCH₃ |
| 30 | " | 2,3-Dibromoallyl | " | COOCH₃ |
| 33 | " | " | " | H |
| 34 | " | 3-Chloroallyl | 2-(1,3-Dioxan-2-yl-)ethyl | COOCH₃ |
| 35 | " | 2-Chloroallyl | " | COOCH₃ |
| 39 | " | 2,3-Dichloroallyl | " | H |
| 40 | " | 2,3-Dibromoallyl | " | H |
| 42 | " | 3-Chloroallyl | 1-(4-Methyl-1,3-dioxan-2-yl-)-2-methyl-propyl | H |
| 43 | " | " | 1-Phenyl-2-(1,3-dioxolan-2-yl-)ethyl | H |
| 45 | " | Allyl | 2-(1,3-Dithiolan-2-yl-)ethyl | H |
| 46 | " | Ethyl | " | H |
| 47 | " | 3-Chloroallyl | " | H |
| 50 | " | " | (4-H)—2,5-Dimethyl-2,3-dihydropyran-2-yl | H |
| 51 | " | Ethyl | 2,5-Dimethyltetrahydropyran-2-yl | H |
| 52 | " | 3-Chloroallyl | 2,5-Dimethyltetrahydropyran-2-yl | H |
| 53 | " | 3-Chloroallyl | (2-H)—5,6-Dihydropyran-3-yl | H |
| 54 | " | Ethyl | (4-H)—2,3-Dihydropyran-2-yl | H |
| 55 | " | Allyl | " | H |
| 56 | " | 3-Chloroallyl | " | H |
| 57 | " | " | Tetrahydropyran-3-yl | H |
| 58 | " | " | Tetrahydropyran-2-yl | H |
| 59 | " | " | (2-H)—2,6-Dimethyl-5,6-dihydrothiopyran-3-yl | H |
| 60 | " | Ethyl | (2-H)—5,6-Dihydrothiopyran-3-yl | COOCH₃ |
| 63 | " | 3-Chloroallyl | (2-H)—5,6-Dihydrothiopyran-3-yl | H |
| 64 | " | Allyl | (2-H)—2,6-Dimethyl-5,6-dihydrothiopyran-3-yl | COOCH₃ |
| 67 | " | 2-Chloroallyl | 4-Methyltetrahydropyran-3-yl | H |
| 69 | Ethyl | Ethyl | " | H |
| 70 | " | Allyl | " | H |
| 73 | Propyl | Butyl | " | H |
| 74 | Ethyl | Ethyl | (2-H)—5,6-Dihydropyran-3-yl | H |
| 75 | " | Allyl | " | H |
| 82 | Propyl | Allyl | 2,5-Dimethyltetrahydropyran-2-yl | H |
| 87 | " | Ethyl | Tetrahydrothiopyran--3-yl | H |
| 88 | " | Allyl | " | H |
| 89 | Ethyl | Ethyl | " | H |
| 90 | " | Allyl | " | H |
| 93 | Propyl | Ethyl | Tetrahydrofuran-3-yl | H |
| 94 | " | Allyl | " | H |
| 95 | Ethyl | Ethyl | " | H |
| 96 | " | Allyl | " | H |
| 97 | Propyl | Ethyl | (6-H)—4,5-Dihydropyran-3-yl | H |
| 98 | " | Allyl | " | H |
| 101 | Ethyl | " | (2-H)—2,6-Dimethyl-5,6-dihydropyran-3-yl | H |
| 102 | " | Ethyl | (2-H)—2,6-Dimethyl-5,6-dihydropyran-3-yl | H |
| 103 | Propyl | " | 2,6-Dimethyltetrahydropyran-3-yl | H |
| 104 | " | Allyl | " | H |
| 105 | Ethyl | Ethyl | " | H |
| 106 | " | Allyl | " | H |
| 107 | Propyl | Ethyl | 1,3-Dioxep-5-yl | H |
| 108 | " | Allyl | " | H |
| 109 | " | Ethyl | 2-(1,3-Dithian-2-yl-)ethyl | H |
| 110 | " | Allyl | " | H |
| 111 | " | 3-Chloroallyl | " | H |

-continued

| Compound no. | R¹ | R² | $X_n$—Y | Z |
|---|---|---|---|---|
| 113 | calcium salt of compound no. 26 | | | |
| 114 | copper salt of compound no. 26 | | | |
| 115 | sodium salt of compound no. 79 | | | |
| 116 | sodium salt of compound no. 19 | | | |
| 117 | calcium salt of compound no. 19 | | | |

The 1H-NMR spectroscopic data ascertained with these compounds are given in the following table. The chemical shifts were referred to tetramethylsilane as internal standard, and are given in δ values (ppm).

The solvent employed was $CDCl_3$; the abbreviations for the signal structures are as follows:
s: singlet
d: doublet
t: triplet
q: quartet
m: multiplet with more than 4 lines

| Compound no. | $\rangle\!=\!\langle$ H     H | | Characteristic signals O—CH₂ | COOCH₃ |
|---|---|---|---|---|
| 1 | — | | 4.09 (q) | 3.75 (s) |
| 2 | — | | 4.51 (d) | — |
| 3 | — | | 4.51 (d) | 3.77 (s) |
| 4 | — | | 4.51 (d) | 3.78 (s) |
| 5 | — | | 4.11 (q) | — |
| 6 | — | | 4.52 (d) | — |
| 7 | — | | 4.51 (d) | 3.76 (s) |
| 8 | — | | 4.08 (q) | — |
| 9 | — | | 4.50 (d) | 3.78 (s) |
| 10 | — | | 4.08 (q) | — |
| 11 | — | | 4.58 (d) | — |
| 12 | — | | 4.09 (q) | 3.74 (s) |
| 13 | — | | 4.54 (d) | 3.78 (s) |
| 14 | — | | — | — |
| 15 | — | | 4.06 (q) | 3.69 (s) |
| 16 | — | | 4.51 (d) | 3.70 (s) |
| 17 | 5.75 (s) | | — | 3.78 (s) |
| 18 | 5.75 (s) | | 4.50 (d) | 3.75 (s) |
| 19 | 5.60 (s) | | 4.10 (q) | — |
| 20 | 4.65 (m) 6.20 (m) | | 4.10 (q) | 3.75 (s)(*) |
| 21 | 4.70 (m) 6.30 (m) | | 4.60 (d) | 3.70 (s) |
| 22 | — | | 4.11 (q) | 3.75 (s) 3.80 (s) |
| 23 | — | | 4.52 (d) | 3.75 (s) 3.80 (s) |
| 24 | — | | 4.12 (q) | — |
| 25 | — | | 4.51 (d) | — |
| 26 | — | | 4.05 (q) | — |
| 31 | — | | 4.50 (m) | — |
| 32 | — | | 4.56 (s) | — |
| 44 | — | | 4.50 | — |
| 68 | — | | 4.89 (s) | — |

(*)The splitting of the ester signals is caused by diastereoisomerism

Application as herbicide may be effected for instance in the form of directly sprayable solutions, powders, suspensions, dispersions, emulsions, oil dispersions, pastes, dusts, broadcasting agents, or granules by spraying, painting, impregnating, atomizing, dusting, broadcasting or watering. The forms of application depend entirely on the purpose for which the agents are being used, but they must ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

The herbicides contain for example from 5 to 95, and especially from 10 to 80, wt% of active ingredient.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

EXAMPLE a 90 parts by weight of compound 1 is mixed with 10 parts by weight of N-methyl-alpha-pyrrolidone. A mixture is obtained which is suitable for application in the form of very fine drops.

EXAMPLE b 10 parts by weight of compound 2 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

EXAMPLE c 20 parts by weight of compound 3 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

EXAMPLE d 20 parts by weight of compound 1 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil.

EXAMPLE e 80 parts by weight of compound 1 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

EXAMPLE f 5 parts by weight of compound 1 is intimately mixed with 95 parts by weight of particulate kaolin. A dust is obtained containing 5% by weight of the active ingredient.

EXAMPLE g 30 parts by weight of compound 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE h 40 parts by weight of compound 1 is intimately mixed with 10 parts of the sodium salt iof a phenolsulfonic acid-urea-formaldehyde condensate, 2 parts of silica gel and 48 parts of water to give a stable aqueous dispersion.

EXAMPLE i 20 parts of compound 1 is intimately mixed with 12 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The action of the novel cyclohexane-1,3-dione derivatives on the growth of plants from the Gramineae family and broadleaved crop plants is demonstrated in the greenhouse experiments and experiments in the open described below. It is also possible in these experiments for crop plants from the Gramineae family to wither or to be heavily damaged. This can be quite desirable in practice, because crop plants can become unwanted plants when they grow in another crop from seed still in the soil, e.g., voluntary barley in winter rape, or sorghum in soybeans.

The vessels employed for the experiments were plastic flowerpots having a volume of 300 cm$^3$, and which were filled with a sandy loam containing about 1.5% humus. In the case of soybeans, peat was added to ensure good growth. The seeds of the test plants were sown shallow, and separately, according to species.

In the preemergence treatment, the active ingredients were applied to the surface of the soil as a suspension or emulsion in water by spraying through finely distributing nozzles. The amount of active ingredient applied in this treatment was equivalent to 3.0 kg/ha.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 15 cm, depending on growth form, before being treated. The application rates for the postemergence treatment varied, depending on the active ingredient and object to be achieved, and were 0.125, 0.25, 0.5 and 1.0 kg of active ingredient per hectare.

For comparison purposes, the following compounds were used (postemergence):

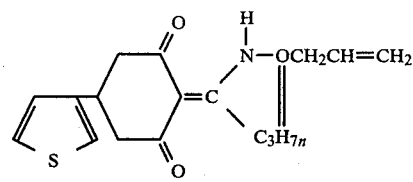

(German Printed Application DE-AS No. 2,439,104) at 0.25 kg/ha, and

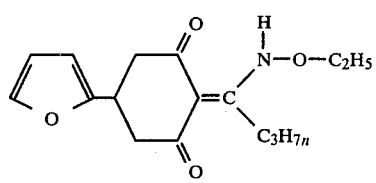

and

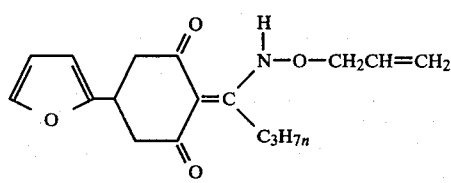

both at 0.25 and 0.5 kg/ha.

The pots were set up in the greenhouse—species from warmer areas at from 20° to 35° C., and species from moderate climates at 10° to 20° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

In the experiments in the open, the agents were emulsified or suspended in water and applied postemergence to small plots by means of a plot spray mounted on a tractor. The application rate was 0.25 kg of active ingredient per hectare. The object was to combat voluntary barley in young winter rape.

The following test plants were employed:

| Botanical Name | Common name |
| --- | --- |
| Alopecurus myosuroides | blackgrass |
| Avena fatua | wild oats |
| Avena sativa | oats |
| Beta vulgaris | sugarbeets |
| Brassica napus | rape seed |
| Bromus tectorum | downy brome |
| Echinochloa crus-galli | barnyardgrass |
| Gossypium hirsutum | cotton |
| Glycine max. | soybeans |
| Hordeum vulgare | barley |
| Lolium multiflorum | annual ryegrass |
| Rottboellia exaltata | itchgrass |
| Setaria spp. | foxtail |
| Sorghum bicolor | sorghum |
| Sorghum halepense | Johnsongrass |
| Triticum aestivum | wheat |
| Zea mays | Indian corn |

The results shows that the novel compounds are suitable, on postemergence application, for combating unwanted plants from the Gramineae family. These may be typical grass weed species, e.g., wild oats (*Avena fatua*), or crop plants from the Gramineae family which, by growing in the wrong place, have become unwanted plants (e.g., Indian corn in a soybean field). Some compounds control unwanted grasses on the one hand, and on the other are excellently tolerated by wheat, which botanically is a member of the grass family, in addition to exhibiting good selectivity in broadleaved crops.

Investigations into the herbicidal action on postemergence application of 0.25 kg/ha of compound no. 26 revealed an average control value of 81 on 9 varieties of grass. A value of 74 was attained by compound no. 24 at the same rate and employing the same method.

The prior art comparative agent A, also applied postemergence at 0.25 kg/ha to the same grass varieties, only had an average action of 52%. The two other comparative agents, B and C, had a herbicidal action which also was weak by comparison.

Broadleaved crop plants, such as cotton (*Gossypium hirsutum*), soybeans (*Glycine max.*), sugarbeets (*Beta vulgaris*) and rape (*Brassica napus*) were completely undamaged by these treatments, or their growth was only impaired to an unsubstantial extent. This means that the novel compounds exhibit a high degree of selectivity for dicotyledon crops. Furthermore, some of the novel compounds, e.g., nos. 31 and 1, when applied at 0.25 kg/ha, combated unwanted grasses such as slender foxtail and panic-grass, while having a selective effect in wheat.

With regard to the herbicidal action, the effect of the novel compounds (e.g., nos. 2, 10, 11, 19, 24 and 26) on plant species from the family of grasses was demonstrated in a series of further experiments.

In the greenhouse experiments, compounds nos. 1, 4, 5, 8, 31, 32, 36 and 37, also applied postemergence, exhibited comparatively good control.

In experiments in the open, compounds nos. 10, 11 and 26, applied postemergence at a rate of 0.25 kg/ha, selectively controlled voluntary barley in rape.

In addition to postemergence effects, positive results were also achieved with the novel compounds on preemergence application in the greenhouse—for example, 3.0 kg/ha of compounds nos. 2, 5, 8, 10, 14, 19, 26, 32, 36, 37, 48, 49, 54, 55, 77 and 78, applied preemergence, had a strong herbicidal action on the grassy plants oats, Italian ryegrass and barnyardgrass. Compounds nos. 1, 3 and 4 also exhibited a considerable herbicidal action on these grass species when applied preemergence in the greenhouse at 3.0 kg/ha.

In view of the fact that the compounds according to the invention are tolerated well, they—or agents containing them— may be used in a large number of crops for removing unwanted plant growth. The application rates may vary from 0.1 to 15 kg/ha and more. The following crop plants may be given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Beta vulgaris spp. esculenta | table beets, red beets |
| Brassica napus var. napus | rape |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |

-continued

| Botanical name | Common name |
| --- | --- |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel cyclohexane-1,3-dione derivatives may be mixed and applied together with prior art cyclohexane-1,3-dione derivatives and with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, etc. Such combinations broaden the spectrum of action. A number of active ingredients which, when combined with the new compounds, give mixtures useful for widely varying applications are given below by way of example:

5-amino-4-chloro-2-phenyl-3(2H)-pyridazinone
5-amino-4-bromo-2-phenyl-3(2H)-pyridazinone
5-amino-4-chloro-2-cyclohexyl-3(2H)-pyridazinone
5-amino-4-bromo-2-cyclohexyl-3(2H)-pyridazinone
5-methylamino-4-chloro-2-(3-trifluoromethylphenyl)-3(2H)-pyridazinone
5-methylamino-4-chloro-2-(3-alpha,alpha,beta,beta-tetrafluoroethoxyphenyl)-3(2H)-pyridazinone
5-dimethylamino-4-chloro-2-phenyl-3(2H)-pyridazinone
4,5-dimethoxy-2-phenyl-3(2H)-pyridazinone
4,5-dimethoxy-2-cyclohexyl-3(2H)-pyridazinone
4,5-dimethoxy-2-(3-trifluoromethylphenyl)-3(2H)-pyridazinone
5-methoxy-4-chloro-2-(3-trifluoromethylphenyl)-3(2H)-pyridazinone
5-amino-4-bromo-2-(3-methylphenyl)-3(2H)-pyridazinone 3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide 3-(1-methylethyl)-1H-pyridino-[3,2-e]-2,1,3-thiadiazin-(4)-one-2,2-dioxide N-(1-ethylpropyl)-2,6-dinitro-3,4-dimethylaniline
N-(1-methylethyl)-N-ethyl-2,6-dinitro-4-trifluoromethylaniline
N-n-propyl-N-β-chloroethyl-2,6-dinitro-4-trifluoromethylaniline
N-n-propyl-N-cyclopropylmethyl-2,6-dinitro-4-trifluoromethylaniline
N-bis-(n-propyl)-2,6-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
bis-(β-chloroethyl)-2,6-dinitro-4-methylaniline
N-ethyl-N-(2-methylallyl)-2,6-dinitro-4-trifluoromethylaniline
3,4-dichlorobenzyl N-methylcarbamate 2,6-di-tert.butyl-4-methylphenyl N-methylcarbamate
isopropyl N-phenylcarbamate
3-methoxyprop-2-yl N-3-fluorophenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoyloxypropionanilide ethyl-N-(3-(N'-phenylcarbamoyloxy)-phenyl)-carbamate
methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate methyl-N-(3-(N'-3-methylphenylcarbamoyloxy)-phenyl)-carbamate
methyl-N-(3-(N'-4-fluorophenylcarbamoyloxy)-phenyl)-carbamate
methyl-N-(3-(N'-3-chloro-4-fluorophenylcarbamoyloxy)-phenyl)-carbamate
ethyl-N-[3-N'-(3-chloro-4-fluorophenylcarbamoxyloxy)-phenyl]-carbamate
ethyl-N-[3-N'-(3,4-difluorophenylcarbamoyloxy)-phenyl]-carbamate
methyl-N-[3-(N'-3,4-difluorophenylcarbamoyloxy)-phenyl]-carbamate methyl N-3-(4'-fluorophenoxycarbonylamino)-phenylcarbamate
ethyl N-3-(2'-methylphenoxycarbonylamino)-phenylcarbamate
methyl N-3-(4'-fluorophenoxycarbonylamino)-phenylthiolcarbamate
methyl N-3-(2',4',5'-trimethylphenoxycarbonylamino)-phenylthiolcarbamate
methyl N-3-(phenoxycarbonylamino)-phenylthiolcarbamate p-chlorobenzyl N,N-diethylthiolcarbamate
ethyl N,N-di-n-propylthiolcarbamate
n-propyl N,N-di-n-propylthiolcarbamate 2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.1.1]-heptylthiolcarbamate
S-(2,3-dichloroallyl)-(2,2,4-trimethylazetidine)-1-carbothiolate
S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate
S-ethyl-(3-methylhexahydro-1-H-azepine-1)-carbothiolate n-propyl N-ethyl-N-n-butylthiolcarbamate
2-chloroallyl N,N-dimethyldithiocarbamate
N-methyldithiocarbamic acid, sodium salt
trichloroacetic acid, sodium salt
alpha,alpha-dichloropropionic acid, sodium salt
alpha,alpha-dichlorobutyric acid, sodium salt
alpha,apha,beta,beta-tetrafluoropropionic acid, sodium salt
alpha-methyl-alpha,beta-dichloropropionic acid, sodium salt
methyl alpha-chloro-beta-(4-chlorophenyl)-propionate
methyl alpha,beta-dichloro-beta-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate 2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate 2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione 3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil 2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-allyloxy-1-(4-bromophenyl)-2-[1',2',4'-triazolyl-(1')]-ethane (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(1-methyl-propyn-2-yl)-2-chloroacetanilide 2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-1-yl-methyl)-2-chloroacetanilide
2-methyl-6-ethyl-N-(pyrazol-1-yl-methyl)-2-chloroacetanilide
2,6-dimethyl-N-(pyrazol-1-yl-methyl)-2-chloroacetanilide
2,6-dimethyl-N-(4-methylpyrazol-1-yl-methyl)-2-chloro-acetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide
2,6-diethyl-N-(propoxyethyl)-2-chloroacetanilide 2-(2-methyl-4-chlorophenoxy)-N-methoxyacetamide
2-(alpha-naphthoxy)-N,N-diethylpropionamide
2,2-diphenyl-N,N-dimethylacetamide
alpha-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
5-acetamido-2,4-dimethyltrifluoromethanesulfone anilide
5-acetamido-4-methyltrifluoromethanesulfone anilide
2-propionylamino-4-methyl-5-chlorothiazole O-(methylsulfonyl)-glycolic acid N-ethoxymethyl-2,6-dimethylanilide
O-(methylaminosulfonyl)-glycolic acid N-isopropylanilide
O-(isopropylaminosulfonyl)-glycolic acid N-but-1-yn-3-yl-anilide
O-(methylaminosulfonyl)-glycolic acid hexamethyleneamide 2,6-dichlorothiobenzamide
2,6-dichlorobenzonitrile 3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
3,5-dibromo-4-hydroxy-O-2-cyano-4-nitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2,4-dichlorophenyl-3'-methoxycarbonyl-4'-nitro-phenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)

(4-bromophenyl)-3,4,5,9,10-pentaazatetracyclo-[5,4,1,O$^{2,6}$,O$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyl-dimethylaminosulfate
2-ethoxy-2,3-dihydro-3,3-dimethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol (salts, esters)
2-sec.butyl-4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate 2-sec.amyl-4,6-dinitrophenol (salts, esters)
1-(alpha,alpha-dimethylbenzyl)-3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1(4-chlorophenyl)-3-methyl-3-but-1-yn-3-yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-(alpha,alpha-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea 1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-fluorophenyl)-3-carboxymethoxy-3-methylurea
1-phenyl-3-methyl-3-methoxyurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea
imidazolidin-2-one-1-carboxylic acid isobutylamide
1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)-pyrazole
2,3,5-trichloropyridinol-(4)

1-methyl-3-phenyl-5-(3'-trifluoromethylphenyl)-pyridone-(4)
1-methyl-4-phenylpyridinium chloride
1,1-dimethylpyridinium chloride
3-phenyl-4-hydroxy-6-chloropyridazine
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione
2-[1-(N-allyloxyamino)-propylidene]-5,5-dimethylcyclohexane-1,3-dione (salts)
2-[1-N-allyloxyamino-butylidene]-5,5-dimethylcyclohexane-1,3-dione (salts)
2-[1-(N-allyloxyamino-butylidene]-5,5-dimethyl-4-methoxycarbonyl-cyclohexane-1,3-dione (salts)
2-chlorophenoxyacetic acid (salts, esters, amides)
4-chlorophenoxyacetic acid (salts, esters, amides)
2,4-dichlorophenoxyacetic acid (salts, esters, amides)
2,4,5-trichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)
methyl alpha-naphthoxyacetate
2-(2-methylphenoxy)-propionic acid (salts, esters, amides)
2-(4-chlorophenoxy)-propionic acid (salts, esters, amides)
2-(2,4-dichlorophenoxy)-propionic acid (salts, esters, amides)
2-(2,4,5-trichlorophenoxy)-propionic acid (salts, esters, amides)
2-(2-methyl-4-chlorophenoxy)-propionic acid (salts, esters, amides)

4-(2,4-dichlorophenoxy)-butyric acid (salts, esters, amides)
4-(2-methyl-4-chlorophenoxy)-butyric acid (salts, esters, amides)
cyclohexyl-3-(2,4-dichlorophenoxy)-acrylate
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-n-butylamino-cyclohexyl-phosphonate
trithiobutylphosphite
O,O-diisopropyl-5-(2-benzosulfonylaminoethyl)-phosphorodithioate
2,3-dihydro-5,6-dimethyl-1,4-dithiin-1,1,4,4-tetraoxide
5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)

(2-chloroethyl)-trimethylammonium chloride
(2-methyl-4-phenylsulfonyl)-trifluoromethanesulfone anilide
1,1-dimethyl-4,6-diisopropyl-5-indanyl ethyl ketone
sodium chlorate
ammonium thiocyanate
calcium cyanamide
2-chloro-4-trifluoromethyl-3'-ethoxycarbonyl-4'-nitrophenyl ether
1-(4-benzyloxyphenyl)-3-methyl-3-methoxyurea
2-[1-(2,5-dimethylphenyl)-ethylsulfonyl]-pyridine-N-oxide
1-acetyl-3-anilino-4-methoxycarbonyl-5-methylpyrazole
3-anilino-4-methoxycarbonyl-5-methylpyrazole
3-tert.butylamino-4-methoxycarbonyl-5-methylpyrazole
N-benzyl-N-isopropyl-trimethylacetamide
methyl 2-[4-(4'-chlorophenoxymethyl)-phenoxy]-propionate
ethyl 2-[4-(5'-bromopyridyl-2-oxy)-phenoxy]-propionate
ethyl 2-[4-(5'-iodopyridyl-2-oxy)-phenoxy]-propionate
n-butyl 2-[4-(5'-iodopyridyl-2-oxy)-phenoxy]-propionate
2-chloro-4-trifluoromethylphenyl-3'-(2-fluoroethoxy)-4'-nitrophenyl ether
2-chloro-4-trifluoromethylphenyl-3-(ethoxycarbonyl)-methylthio-4-nitrophenyl ether
2,4,6-trichlorophenyl-3-(ethoxycarbonyl)-methylthio-4-nitrophenyl ether
2-[1-(N-ethoxamino)-butylidene]-5-(2-ethylthiopropyl)-3-hydroxy-cyclohex-2-en-1-one (salts)
2-[1-(N-ethoxamino)-butylidene]-5-(2-phenylthiopropyl)-3-hydroxy-cyclohex-2-ene-1-one (salts)
ethyl-4-[4-(4'-trifluoromethyl)-phenoxy]-pentene-2-carboxylate
2-chloro-4-trifluoromethyl-3'-methoxycarbonyl-4'-nitrophenyl ether
2,4-dichlorophenyl-3'-carboxy-4-nitrophenyl ether (salts)

4,5-dimethoxy-2-(3-alpha,alpha,beta-trifluoro-beta-bromoethoxyphenyl)-3-(2H)-pyridazinone
2,4-dichlorophenyl-3'-ethoxy-ethoxy-ethoxy-4'-nitrophenyl ether
2,3-dihydro-3,3-dimethyl-5-benzofuranyl-ethane sulfonate
N-[4-methoxy-6-methyl-1,3,5-triazin-2-yl-aminocarbonyl]-2-chlorobenzene sulfonamide
1-(3-chloro-4-ethoxyphenyl)-3,3-dimethylurea
ethyl 2-methyl-4-chlorophenoxy-thioacetate
2-chloro-3,5-diiodo-4-acetoxy-pyridine
1-{4-[2-(4-methylphenyl)-ethoxy]-phenyl}-3-methyl-3-methoxyurea
2,6-dimethyl-N-(pyrazol-1-yl-methylenoxymethyl)-2-chloroacetanilide
2-methyl-6-ethyl-N-(pyrazol-1-yl-methylenoxymethyl)-2-chloroacetanilide
1-(alpha-2,4-dichlorophenoxypropionic acid)-3-(O-methylcarbamoyl)-anilide
1-(alpha-2-bromo-4-chlorophenoxypropionic acid)-3-(O-methylcarbamoyl)-anilide
2-methyl-6-ethyl-N-(pyrazol-1-yl-ethylenoxymethyl)-2-chloroacetanilide
methyl-N-dichlorofluoromethylsulfenyl-[3-(N'-dichlorofluoromethylsulfenyl-N'-phenylcarbamoyl-oxy)-phenyl]-carbamate
methyl-N-dichlorofluoromethylsulfenyl-[3-(N'-dichlorofluoromethylsulfenyl-N'-3-methylphenylcarbamoyl-oxy)-phenyl]-carbamate
N-(pyrazol-1-yl-methyl)-pyrazol-1-yl-acetic acid-2,6-dimethylanilide
N-(pyrazol-1-yl-methyl)-1,2,4-triazol-1-yl-acetic acid-2,6-dimethylanilide 2-(3-trifluoromethylphenyl)-4H-3,1-benzoxazin-4-one
2-(2-thienyl)-4H-3,1-benzoxazin-4-one
2-(3-pentafluoroethoxyphenyl)-4H-3,1-benzoxazin-4-one
2-(3-trifluoromethylthio-phenyl)-4H-3,1-benzoxazin-4-one
2-(3-difluorochloromethoxyphenyl)-4H-3,1-benzoxazin-4-one 5-nitro-2-(3-trifluoromethyl-phenyl)-4H-3,1-benzoxazin-4-one
5-chloro-2-(3-trifluoromethoxyphenyl)-4H-3,1-benzoxazin-4-one
5-chloro-2-[(3-alpha-alpha-beta-beta)-tetrafluoroethoxyphenyl]-4H-3,1-benzoxazin-4-one
5-fluoro-2-[(3-alpha-alpha-beta-beta)-tetrafluoroethoxyphenyl]-4H-3,1-benzoxazin-4-one
5-chloro-2-(4-difluorochloromethoxyphenyl)-4H-3,1-benzoxazin-4-one
5-fluoro-2-(4-difluorochloromethoxyphenyl)-4H-3,1-benzoxazin-4-one
5-fluoro-2-(phenyl)-4H-3,1-benzoxazin-4-one
5-fluoro-2-(3-difluoromethoxyphenyl)-4H-3,1-benzoxazin-4-one
5-chloro-2-(phenyl)-4H-3,1-benzoxazin-4-one
3-(3,5-dichlorophenyl)-4-methoxycarbonyl-5-methyl-pyrazole
3-(3-chlorophenyl)-4-methoxycarbonyl-5-methyl-pyrazole
3-(3-fluorophenyl)-4-methoxycarbonyl-5-methyl-pyrazole
1-acetyl-3-(3-fluorophenyl)-4-methoxycarbonyl-5-methylpyrazole
1-acetyl-3-(3-chlorophenyl)-4-methoxycarbonyl-5-methylpyrazole
1-acetyl-3-(3-bromophenyl)-4-methoxycarbonyl-5-methylpyrazole
1-acetyl-3-(3,5-dichlorophenyl)-4-methoxycarbonyl-5-methylpyrazole
1-acetyl-3-thienyl-4-methoxycarbonyl-5-methyl-pyrazole
methyl N-3-chloro-4-isopropylphenyl-thiolcarbamate
methyl N-3-methyl-4-fluorophenyl-thiolcarbamate
methyl N-3-chloro-4-isopentylphenyl-thiolcarbamate
methyl N-3-chloro-4-difluoromethoxyphenyl-thiolcarbamate
methyl N-3-chloro-4-(1-chloroisopropyl)-phenyl-thiolcarbamate
1-(2-fluorophenyl)-3-methyl-5-iminoimidazolidin-2-one
1-(3-isopropylphenyl)-3-methyl-5-iminoimidazolidin-2-one
1-(4-isopropylphenyl)-3-methyl-5-iminoimidazolidin-2-one
1-[3-(1,1,2,2-tetrafluoroethoxy)-phenyl]-3-methyl-5-iminoimidazolidin-2-one
1-(3,4-dichlorophenyl)-3-methyl-5-iminoimidazolidin-2-one
1-(3,4-difluorophenyl)-3-methyl-5-iminoimidazolidin-2-one
6-methyl-3-methoxy-5,6-dihydro-1,2,4,6-thiatriazin-5-one-1,1-dioxide
6-methyl-3-methoxy-5,6-dihydro-1,2,4,6-thiatriazin-5-one-1,1-dioxide, sodium salt
6-n-propyl-3-methoxy-5,6-dihydro-1,2,4,6-thiatriazin-5-one-1,1-dioxide
6-methyl-3-ethoxy-5,6-dihydro-1,2,4,6-thiatriazin-5-one-1,1-dioxide
6-n-propyl-3-ethoxy-5,6-dihydro-1,2,4,6-thiatriazin-5-one-1,1-dioxide, sodium salt
6-methyl-3-isopropoxy-5,6-dihydro-1,2,4,6-thiatriazin-5-one-1,1-dioxide
6-n-propyl-3-isopropoxy-5,6-dihydro-1,2,4,6-thiatriazin-5-one-1,1-dioxide
6-isopropyl-3-sec-butoxy-5,6-dihydro-1,2,4,6-thiatriazin-5-on-1,1-dioxide, sodium salt
N-3'-(2''-chloro-4''-trifluormethylphenoxy)-6'-nitrobenzoylanthranilic acid
methyl N-3'-(2''-chloro-4''-trifluoromethylphenoxy)-6'-nitrobenzoylanthranilate
N-3'-(2''-chloro-4''-trifluoromethylphenoxy)-6'-nitrobenzoylanthranilic acid, sodium salt
N-3'-(2''-chloro-4''-trifluoromethylphenoxy)-6'-nitrobenzoyl-3-chloroanthranilic acid
N-3'-(2''-chloro-4''-trifluoromethylphenoxy)-benzoyl-3-chloroanthranilic acid
N-3'-(2''-chloro-4''-trifluoromethylphenoxy)-benzoyl-3-methylanthranilic acid
N-3'-(2''-chloro-4''-trifluoromethylphenoxy)-benzoylanthranilic acid
N-3'-(2'',4''-dichlorophenoxy)-6'-nitrobenzoylanthranilic acid
N-[3'-(2''-chloro-4''-trifluoromethylphenoxy)-6'-nitrophenyl]-4H-1,3-benzoxazin-4-one
N-[3'-(2''-chloro-4''-trifluoromethylphenoxy)-6'-nitrophenyl]-4H-1,3-8-methoxybenzoxazin-4-one 5-chloro-2-(3-trifluoromethyl-phenyl)-4H-3,1-benzoxazin-4-one
5-fluoro-2-(3-trifluoromethyl-phenyl)-4H-3,1-benzoxazin-4-one 5-fluoro-2-(3-difluorochloromethyl-phenyl)-4H-3,1-benzoxazin-4-one 5-chloro-2-(3-difluorochloromethyl-phenyl)-4H-3,1-benzoxazin-4-one 1-[5-(3-fluorobenzylthio)-thiadiazolyl-2]-1-methyl-3-methylurea It may also be useful to apply the novel compounds, either on their own or combined with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A cyclohexadione derivative of the formula

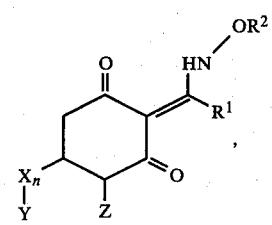

where $R^1$ is alkyl of 1 to 4 carbon atoms, $R^2$ is alkyl of 1 to 4 carbon atoms, alkenyl of 3 or 4 carbon atoms, alkynyl of 3 or 4 carbon atoms or haloalkenyl of 3 to 4 carbon atoms and 1 to 3 halogen atoms, X is straight-chain or branched alkylene of 1 to 5 carbon atoms, which is unsubstituted or substituted by phenyl, n is 0 or 1, Y is, selected from the group consisting of tetrahydropyranyl, dihydropyranyl, methyltetrahydropyranyl, dioxanyl, dioxolanyl, dithiolanyl, dihydrothiopyranyl, tetrahydrothiopyranyl, dimethyldihydropyranyl, tetrahydrofuranyl and dimethyldihydrothiopyranyl, and Z is hydrogen or methoxycarbonyl, or a salt thereof.

2. A process for combating the growth of unwanted plants, wherein the plants or the soil are treated with a cyclohexanedione derivative of the formula

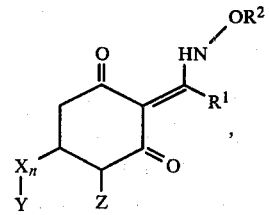

where $R^1$ is alkyl of 1 to 4 carbon atoms, $R^2$ is alkyl of 1 to 4 carbon atoms, alkenyl of 3 or 4 carbon atoms, alkynyl of 3 or 4 carbon atoms or haloalkenyl of 3 or 4 carbon atoms and 1 to 3 halogen atoms, X is straight-chain or branched alkylene of 1 to 5 carbon atoms, which is unsubstituted or substituted by phenyl, n is 0 or 1, Y is, selected from the group consisting of tetrahydropyranyl, dihydropyranyl, methyltetrahydropyranyl, dioxanyl, dioxolanyl, dithiolanyl, dihydrothiopyranyl, tetrahydrothiopyranyl, dimethyldihydropyranyl, tetrahydrofuranyl and dimethyldihydrothiopyranyl, and Z is hydrogen or methoxycarbonyl, or a salt thereof.

3. A cyclohexanedione derivative selected from the group consisting of 2-(1-ethoxyaminobutylidene)-5-[3-(4-methyltetrahydropyranyl]-cyclohexane-1,3-dione, 2-(1-allyloxyaminobutylidene)-5-[3-(4-methyltetrahydropyranyl)]-cyclohexane-1,3-dione, and 2-(1-ethoxyaminobutylidene)-5-[3-(2H)-5,6-dihydropyranyl]-cyclohexane-1,3-dione.

4. A cyclohexanedione derivative of the formula I as set forth in claim 1, which is 2-(1-ethoxyaminobutylidene)-5-(3-tetrahydropyranyl)-cyclohexane-1,3-dione.

5. A cyclohexanedione derivative of the formula I as set forth in claim 1, which is 2-(1-ethoxyaminobutylidene)-5-(3-tetrahydrothiopyranyl)-cyclohexane-1,3-dione.

6. A cyclohexanedione derivative of the formula I as set forth in claim 1, which is 2-(1-ethoxyaminopropylidene)-5-(3-tetrahydrothiopyranyl)-cyclohexane-1,3-dione.

* * * * *

UNITED STATES PATENT AND TRADEMARK OFFICE
CERTIFICATE OF CORRECTION

PATENT NO. : 4,422,864
DATED : December 27, 1983
INVENTOR(S) : Rainer BECKER et al.

It is certified that error appears in the above-identified patent and that said Letters Patent is hereby corrected as shown below:

Claim 1, column 25, line 17, change "cyclohexadione" to --cyclohexanedione--.

Signed and Sealed this

Third Day of April 1984

[SEAL]

Attest:

GERALD J. MOSSINGHOFF

Attesting Officer

Commissioner of Patents and Trademarks